United States Patent [19]

Salera et al.

[11] 3,933,149

[45] Jan. 20, 1976

[54] ANISOTHERMAL DIFFERENTIATOR

[76] Inventors: Edmond A. Salera, 714 Surf View Drive, Santa Barbara, Calif. 93109; Edmond E. Salera, 1522 Centinela Ave., Los Angeles, Calif. 90025

[22] Filed: Apr. 18, 1974

[21] Appl. No.: 461,854

[52] U.S. Cl. ............... 128/2 H; 73/340; 73/342; 73/362 AR
[51] Int. Cl.² .................. A61B 5/00; G01K 7/24
[58] Field of Search ........ 128/24; 73/340, 341, 342, 73/362 AR

[56] References Cited
UNITED STATES PATENTS

| | | | |
|---|---|---|---|
| 1,648,939 | 11/1927 | Evins | 128/2 H |
| 1,648,942 | 11/1927 | Hayman | 128/2 H |
| 2,661,733 | 12/1953 | Polsky | 128/2 H |
| 2,802,925 | 8/1957 | Von Seelen et al. | 73/362 AR |
| 3,308,667 | 3/1967 | Pearlman | 128/2 H |
| 3,402,378 | 9/1968 | Catlin et al. | 73/362 AR |
| 3,485,102 | 12/1969 | Glick | 128/2 H |
| 3,570,312 | 3/1971 | Krieth | 73/362 AR |
| 3,681,993 | 8/1972 | Campton et al. | 73/362 AR |
| 3,688,581 | 9/1972 | Quernec | 73/362 AR |
| 3,699,813 | 10/1972 | Lamb | 128/2 H |
| 3,765,244 | 10/1973 | Brzezinski | 73/362 AR |

FOREIGN PATENTS OR APPLICATIONS

| | | | |
|---|---|---|---|
| 271,100 | 12/1962 | Australia | 128/2 H |

*Primary Examiner*—Richard A. Gaudet
*Assistant Examiner*—Lee S. Cohen
*Attorney, Agent, or Firm*—William W. Haefliger

[57] ABSTRACT

Local body heat sensing instrumentation comprises
a. a probe including a tip having a surface shaped for application in heat transfer proximity with a patient's body, the tip consisting of material characterized as electrically insulative and heat conductive, and
b. electrically energizable means carried to detect heat transfer between said surface and the source via said material.

17 Claims, 9 Drawing Figures

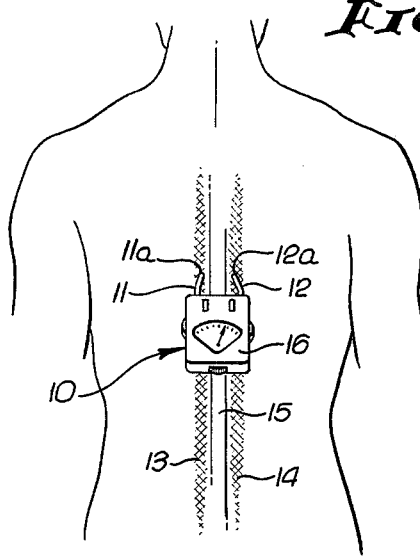
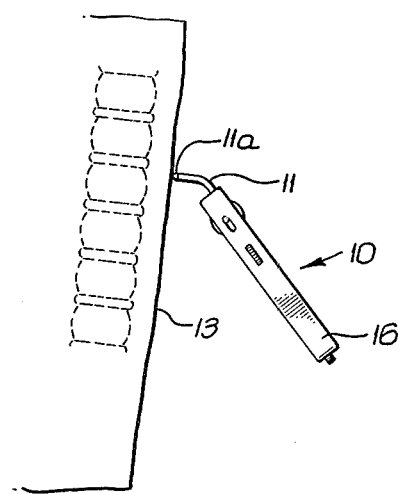
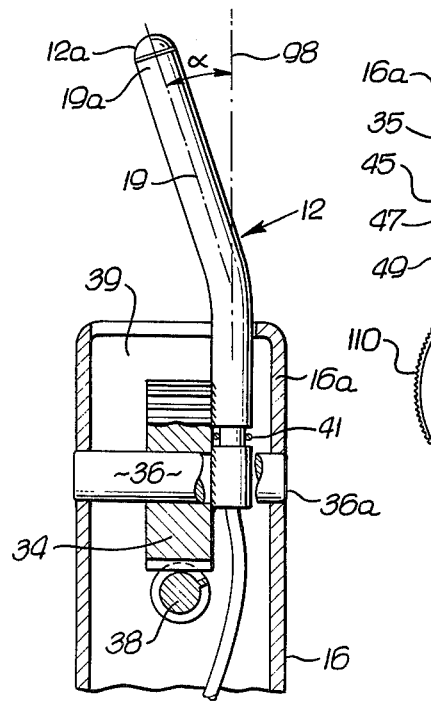
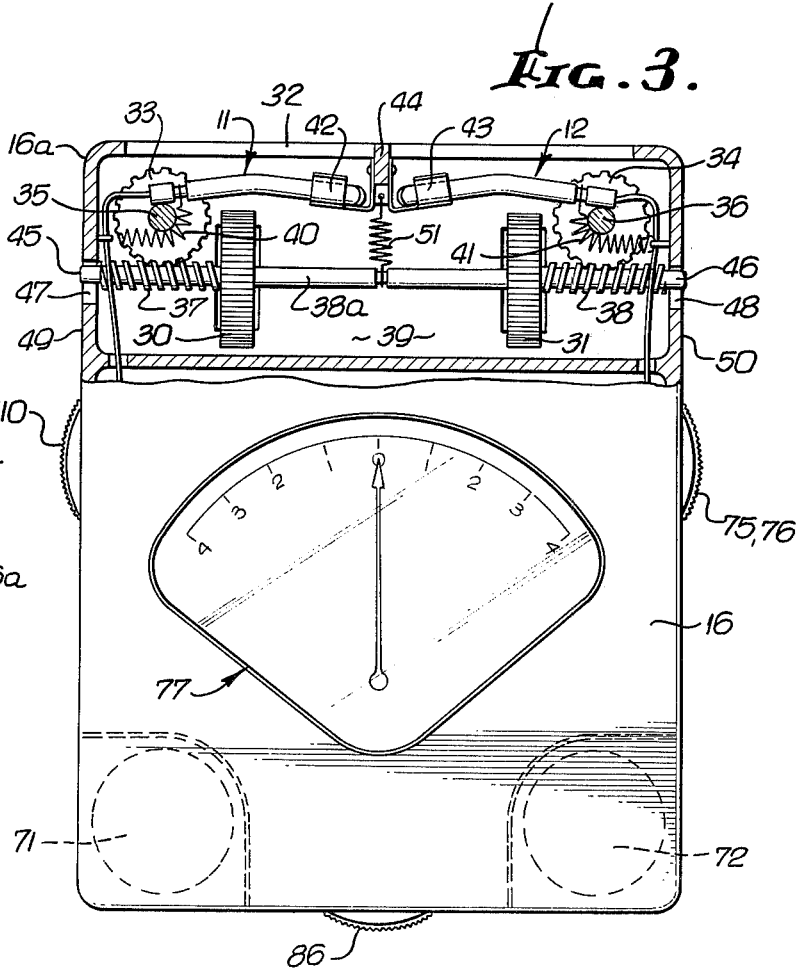

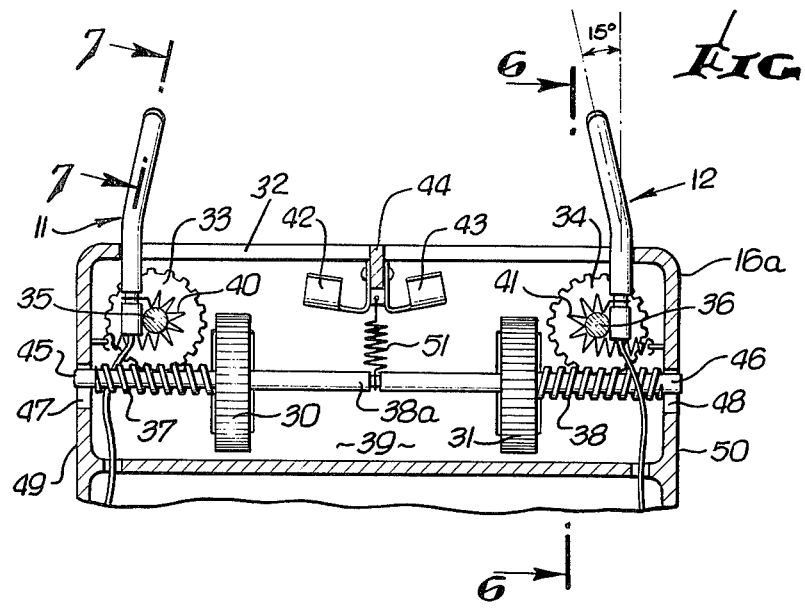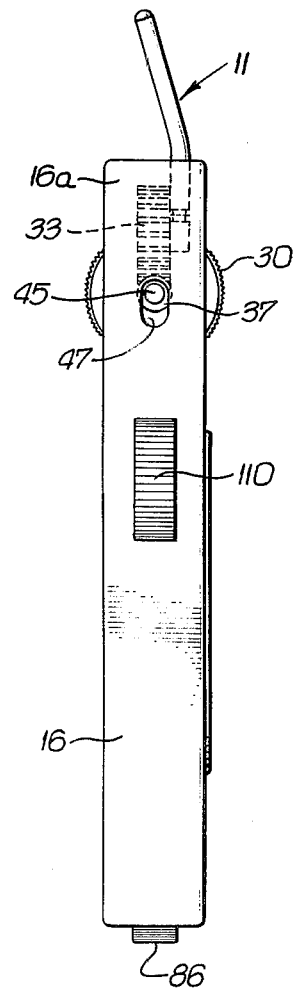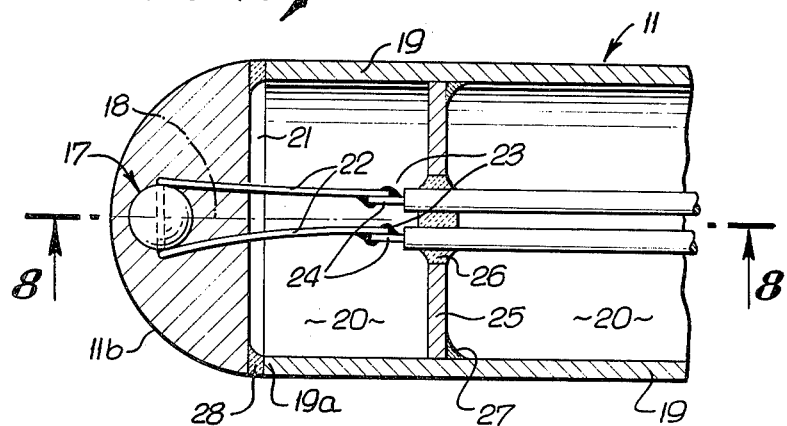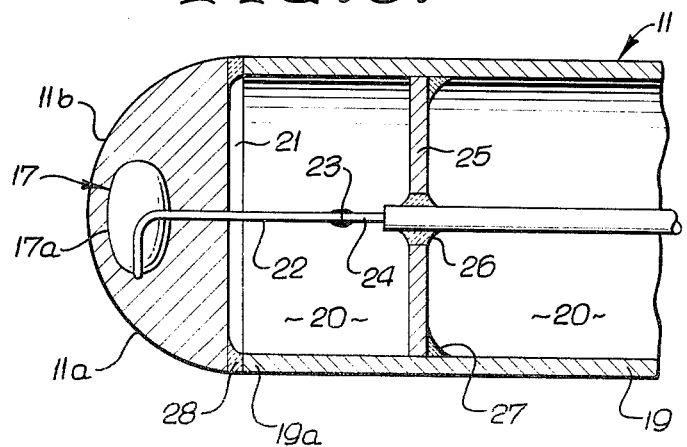

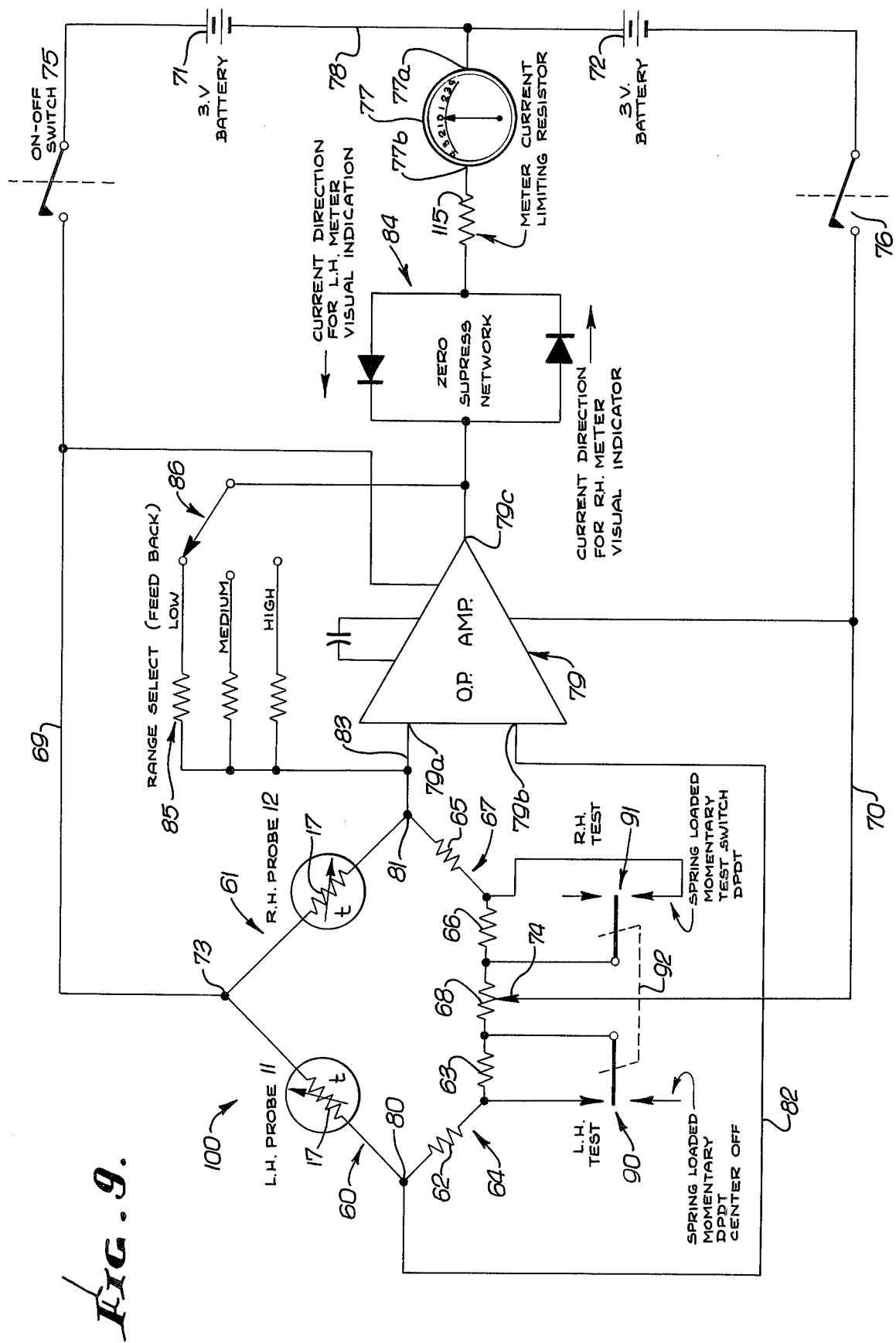

ANISOTHERMAL DIFFERENTIATOR

BACKGROUND OF THE INVENTION

This invention relates generally to instrumentation for sensing local areas or zones of patient body heat, and more particularly concerns such instrumentation effective to sense differential heating of local body areas, as for example skin areas proximate the spinal column.

There is a need for an easily usable, accurate, pocket-sized device that will operate to detect differential heating of patient skin zones. In this regard, it is found that the temperatures of such zones proximate sub-surfaces tissue or muscles in spasm, or sites of bruising or injury are slightly higher than the temperatures of uninjured tissue zones. In particular, there is need for such a device which may be readily applied along the spinal column of a patient to isolate zones along the vertebra which may be in spasm, so that such areas may be investigated.

SUMMARY OF THE INVENTION

It is a major object of the invention to provide instrumentation fulfilling the above need, and also providing additional advantages in construction and operation, as will appear. Basically, the instrument comprises:

a. a probe including a trip having a surface shaped for application in heat transfer proximity with a patient's body, the tip consisting of material characterized as electrically insulative and heat conductive, and b. electrically energizable means carried to detect heat transfer between said surface and the source via said material.

As will appear, a second probe may also be provided on a carrier, the probes located, when extended, to straddle the patient's spinal column along his back; actuator means is typically provided on the carrier to deploy and retract the probes; and thermistors may be used in unusually advantageous manner within the probe tip material to detect the described heat transfer.

Additional objects and advantages include the provision of special probe tip material as will be described; the use of hollow elongated metallic supports associated with the probes and supporting the described tips, there being heat sinks associated with such supports and the thermistor leads extending within the supports; the provision of worm gears to rotate the probes in unison between retracted and deployed position, with thumb-wheel operated worms meshing with the worm gears; and additional structure as will be described to aid in such deployment and retraction.

These and other objects and advantages of the invention, as well as the details of an illustrative embodiment, will be more fully understood from the following description and drawings, in which:

DRAWING DESCRIPTION

FIG. 1 is an elevation showing use of instrumentation embodying the invention;

FIG. 2 is an enlarged side elevation showing use of the FIG. 1 instrumentation;

FIG. 3 is an enlarged frontal view of FIG. 1 instrumentation, partly broken away to show interior details;

FIG. 4 is a fragmentary view of a portion of the FIG. 3 instrument, showing probes in extended, active positions;

FIG. 5 is a side elevation of the instrument, with probes extended as in FIG. 4;

FIG. 6 is an enlarged section on lines 6—6 of FIG. 4;

FIG. 7 is an enlarged section on lines 7—7 of FIG. 4;

FIG. 8 is a section on lines 8—8 of FIG. 7; and

FIG. 9 is a circuit diagram.

DETAILED DESCRIPTION

Referring first to FIGS. 1 and 2, instrumentation is shown at 10 for sensing differential heating of local body areas or zones. For example, such instrumentation may incorporate a pair of like probes as at 11 and 12 and means thereon to effect heat transfer between the probes and a patient's body zones toward which the probes are respectively applied. In the sketches, the illustrated probes include tips 11a and 12a contacting the skin zones 13 and 14 which run vertically at opposite sides of, and closely straddling, the central spinal column zone 15. The instrumentation includes a carrier in the form of a housing 16 from which the two probes project in extended or deployed positions. As will appear, the probes may also have retracted positions relative to the carrier, one example being seen in FIG. 3, to be described. It is found that differential heating of opposite sections of the zones 13 and 14 occurs at loci of spinal injury, muscle spasm or similar difficulties; that such differential heating can be detected as the probes are run vertically along the zones 13 and 14; and therefore the loci of such zone sections can be determined with accuracy through use of the instrumentation 10. The located sections can then be investigated.

Turning to FIGS. 3–8, a typical probe 11 or 12 includes a tip 11a or 12a having a surface shaped for application in heat transfer proximity with a patient's body, the tip consisting of material characterized as electrically insulative and heat conductive; further, electrically energizable means is carried to detect heat transfer between the tip surface and the surface via such material. In the example, the electrically energizable means comprises a thermistor bead embedded in the tip material, as seen in FIGS. 7 and 8, the tip surface 11b is outwardly convex, and the bead is elongated and has an elongated convex surface 17a oriented to be outwardly convex toward the tip surface 11b. Also, the bead is generally centered in the illustrated hemispherical tip so that the thickness of the tip material between the surfaces 17a and 11b at the central axis 18 is less than the bead thickness. As a result, the tip size is minimized, in relation to the size of the thermistor enabling minimum friction skin interface contact area (this is highly desirable in skin areas where folds or wrinkles occurs); also, rapid and efficient heat transfer between the thermistor and tip surface 11b is promoted, the lens effects of the proximate and curved surfaces 17a and 11b enhancing this result. Accordingly, response time to skin temperature changes is minimized. Further, the tip material protects the thermistor from degradation which might result from contact with skin acids, alkali and abrasive debris. The tip material consists of a formable, semi-heat conductive plastic that is also electrically non-conductive, or any refractory that is ceramic in nature, it being the objective that the material be semi heat-conductive and electrically non-conductive, to permit rapid heat transfer and also provide electrical isolation for the bare thermistor and it's two electrical conductor leads. One example of a suitable material is polymerized epoxy resin containing dispersed finely divided aluminum particles in the form of a powder, such as used in the manufacture of aluminum paint, wherein the aluminum particles enhance the thermal conductivity of the material, while the epoxy resin and the hardener provide structure as well as electrical isolation. Such heat conductive epoxies are well known. Another example of a usable carrier material is a refractory substance, for example is comprised of refractory particulate matter (such as alumina and binder mixed with water and which becomes a solid after heat treatment. A source of such material is AREMCO Products Inc., Briarcliff Manor, N.Y. Any refractory composed and compounded to conduct heat in a manner more favorably than glass would give good results.

As mentioned above, semi heat-conductive materials are used in contrast to very efficient heat conductors, such as metals for specific reasons. The semi heat-conductive material favorably retains the thermal energy in the immediate vicinity of the thermistor bead assembly, because the conductance of the material is relatively poorer than metal and this feature is employed to inhibit the conductance of thermal energy from the bead 17 to a metallic support for the tip. In this regard each probe includes a hollow, elongated, metallic support 19, as for example a metal tube. As seen in FIGS. 7 and 8, the support 19 contains an internal cavity 20 containing ambient dead (or non-flowing) air having poor thermal conductivity, such air contacting the inner side 21 of the tip to inhibit loss of heat in the tip and from that side. Also, the exposed fine wire thermistor leads 22 emerge from the tip material centrally of the support tube 19 to extend within the dead air space 20 toward their electrical bond junctions at 23 with the exposed ends of heavier and stronger leads 24, which may be insulated as shown. Leads 24 are positioned centrally within the support 19 as by the disc type spacer 25, there being a suitable bonding material 26 carried by the disc and passing the leads 24 while bonding them to the disc. Accordingly, strain relief is provided, in that stressing of the exposed fine thermistor leads 22 is minimized. Disc 25 is suitably bonded at 27 to the support 19.

It will be noted that the terminal 19a of support 19 is suitably bonded, as at 28, to the annular periphery of the generally hemisperical tip material; accordingly, terminal 19a has maximum spacing from the thermistor 17, so that heat conductance or loss to the support 19 is minimized. Conversely, when the probe is deployed into a cooler area of the skin, the concentration of thermal energy in the thermistor and in the tip material 11a is quickly and efficiently conducted into the cooler skin area, because the thermal energy has been confined, favorably, to relatively small volumetric region.

At this point, attention is called to the importance and reason for the metal support 19. If any thermal energy does reach the latter, such energy can be rapidly dispersed because of the excellent thermal conductivity of the support. In this manner, and in view of the heat transfer properties of the tip, a reasonably short response time is provided even though some of the thermal energy may become temporarily stored in the support metal.

With the above arrangement, the response time of the device, from some maximum sensed condition to zero null, is approximately one order of magnitude better than when a heat insulative material is used for the support 19.

The invention also contemplates the provision of actuator means on the carrier and connected with the probes to retract them from active positions (as for example appear in FIGS. 1, 2, 4, 5 and 6) into retracted positions close to the carrier (as for example is seen in FIG. 3). In this regard, the actuator means may for example include manually operable rotors, such as left and right thumb wheels 30 and 31, one for each probe and structure responsive to manual turning of the rotors to displace or return the deployed probes back toward the carrier, and vice versa.

In the example, the carrier may include a forward housing section 16a having a front opening 32, to receive the probes. Worm gears 33 and 34 are pivotally supported at 35, 36 and 36a in the housing section 16a, and are integrally connected, respectively, with the probes 11 and 12 for rotating the probes between extended and retracted positions. For this purpose, the probes may be connected to the worm gears 33 and 34, as shown, and the metal gears may have heat transfer contact or connection with the probe metal shanks to act as heat sinks therefor.

Two worms 37 and 38 are located in the interior 39 of the housing section 16a to mesh with the respective worm gears 33 and 34, the worms typically having a common lateral axis. A central return spring 51 has opposite ends attached to the lateral shaft 38a and to structure 44, so as to yieldably urge the shaft 38a, and worms forwardly into operative engagement with the worm gears. The thumb wheels 30 and 31 are carried by lateral shaft extent 38a between and integral with the worms, so as to rotate the worms 37 and 38 as the thumb wheels are turned. Probe retraction springs (tension springs) 40 and 41 are operatively connected with the probes to yieldably resist rotation of the probes to extended position, i.e. to yieldably maintain the probes in retracted positions, as seen in FIG. 3. One end of each spring is attached to a probe in offset relation to its associated pivot pin, the spring partially wraps about the pin, and the opposite end of the spring attaches to the housing, as shown. The thumb wheels 30 and 31 may be insulated to be thermally isolated from the probes.

Isothermal means is provided on the carrier to be contacted by the probe tips in their retracted positions, so that both tips when stored, are kept at the same temperature. For this purpose, metal clips may be provided at 42 and 43 in the housing interior 39 to be contacted by the retracted probe metal shanks. The clips have interconnection as at 44 to remain at the same temperature. Accordingly, any extraneous thermal condition existing in the probes in use can be purged by simply retracting the probes to contact the clips or "heat sinks".

It should also be noted that the worm end shafts 45 and 46 are received in longitudinal slot bearings 47 and 48 in the housing side walls 49 and 50, respectively. This allows for rearward thumb pressure on the wheels 30 and 31 to disengage the worms from the worm gears which in turn allows the probe return springs to automatically return the probes to the stored condition. In this manner, the probes may be returned to the stored position without having to rotate the thumb wheels 30 and 31. If it is desirable not to use the automatic feature the probes can be returned to the stowed condition manually by rotating the wheels 30 and 31 in the opposite direction from that which was used to extend them to the deployed position.

Turning to FIG. 9, the thermistors 17 in the two probes 11 and 12 are incorporated in the legs 60 and 61 of a resistance bridge 100, as indicated, there being other resistors 62 and 63 in leg 64 and resistors 65 and 66 in leg 67. A trimming resistor 68 interconnects legs 64 and 67. Leads 69 and 70 from batteries 71 and 72 connect with the bridge at location 73 and via wiper 74 in sliding contact with trim resistor. Ganged on-off power switches 75 and 76 are provided in series with leads 69 and 70.

A meter 77 is located on the carrier and has one terminal 77a connected with the battery interconnection lead 78. In addition an operational amplifier 79 has inputs 79a and 79b connected with the bridge points 80 and 81 via leads 82 and 83, and the amplifier output 79c is connected with the meter input 77b via zero suppress network 84, and meter current limiting resistor 115 as shown. Various resistors 85 of different ohm rating may be selectively connected in feedback relation across the amplifier by switch 86, to select the operating range desired, i.e. low, medium or high. See switch 86 in FIG. 3, also.

Test switches 90 and 91 are connectible across the resistors 63 and 66, respectively, and gang connected at 92. When both are closed upwardly, as by deflection of switch knob 110 seen in FIG. 3, resistor 63 is shorted, and the metal deflects to one side of zero; and when both are closed downwardly, resistor 66 is shorted, and the meter deflects to the opposite side of zero. The circuitry is "zero'd" by adjustment of wiper 74, with both probes retracted, the on-off switches 75 and 76 being closed.

One useful amplifier 79 is Model LM308 a product of the National Semiconductor Corporation. A useful meter movement is the Parker Meter Movement, a product of Airpax Electronics, Fort Lauderdale, Fla.

Finally, as seen in FIG. 6, the end portion 19a of each support 19 is angled at $\alpha$ about 17° from the probe axis 98 parallel to main surfaces of the receptacle 16, to provide a favorable viewing angle of the instrument visual indicating meter face and instrument controls, while the instrument is in use. Also, in addition to the angle $\alpha$, the individual probe end portions 19a may be rotated approximately 15° inwards toward one another, in order to maintain relative contact points of tangency when the instrument and the probes are deployed for use in the region of the patient's neck and it's attendant surface curvatures.

We claim:

1. In local body heat sensing instrumentation, the combination comprising
   a. first and second probes each including a tip having a frontwardly exposed surface shaped for application in heat transfer proximity with a patient's body, the tip consisting of material characterized as electrically insulative and heat conductive,
   b. first and second electrically energizable means carried by the respective probes to detect heat transfer between said surface and the source via said material, said frontwardly exposed surface of each tip being generally convex,
   c. each probe including an openly hollow and forwardly elongated support, said tip confined at the forward end of said support, said tip having a rearward surface facing and exposed to the hollow interior of the support, the outer extent of the tip connected to the support, each said means embedded in the tip material between said front and rear surfaces,
   d. a carrier from which the probes extend in active positions to locate the tips for engaging a human patient's body, the carrier including a housing, there being rotary means including worm gear means on the carrier and supporting the probes for rotation between extended positions outside the housing and retracted positions inside the housing, there also being worm means on the carrier and meshing with the worm gear means, and manually operable means to rotate the worm means, and
   e. recording means electrically connected with said electrically energizable means.

2. The combination of claim 1 wherein said recording means comprises a meter carried by the carrier and is electrically connected with said electrically energizable means, the probes extending from the carrier in active positions to locate the tips for engaging a human patient's back so as to closely straddle the central spinal column zone.

3. The combination of claim 1 wherein each said electrically energizable means comprises a thermistor bead embedded in said material.

4. The combination of claim 3 including an electrical bridge incorporating said thermistor beads, said recording means comprising a meter on the carrier, a zero suppression network, and an operational amplifier having inputs connected with bridge output points and an output connected with the meter via said zero supression network.

5. The combination of claim 4 wherein the bridge includes two resistors respectively in two arms of the bridge, there being shorting switches respectively connectible across the two resistors.

6. The combination of claim 3 wherein the bead has an elongated convex surface oriented toward said tip surface which is also convex in a direction away from the bead.

7. The combination of claim 1 wherein said material consists of a solid resin, and including heat conducting metallic particles dispersed throughout the resin.

8. The combination of claim 1 wherein said material consists of a refractory substance.

9. The combination of claim 1 wherein the hollow elongated supports for said tips are metallic, there being wires extending within the support hollows to the electrically energizable means, circuitry including said recording means electrically connected with the wires, and there being heat sink means coupled in heat transfer relation with the supports.

10. The combination of claim 9 wherein said heat sink means comprises rotary gears respectively connected with the supports to rotate therewith.

11. The combination of claim 1 wherein each probe includes an angularly deflected end portion carrying one of the tips.

12. In local body heat sensing instrumentation, the combination comprising
   a. first and second probes each including a tip having a surface shaped for application in heat transfer proximity with a patient's body, the tip consisting of material characterized as electrically insulative and heat conductive,
   b. electrically energizable means carried by the probes to detect heat transfer between said surface and the source via said material, and c. a carrier for said probes and from which the probes extend in active positions to locate the tips for engaging a human patient's back so as to closely straddle central spinal column zone, the carrier including a housing section having a front opening to receive the probes, there being two worm gears each of which is integrally connected with a probe end portion for rotating the probe between extended position outside the housing section and retracted position inside the housing section, two worms respectively meshing with the two worm gears within said housing section, thumb wheels connected with the worms to rotate same, and probe retraction springs operatively connected with the probes to yieldably resist rotation of the probes to extended position, and d. recording means electrically connected with said electrically energizable means.

13. The combination of claim 12 including guide means for allowing disengagement of the worms from the worm gears in response to retraction pressure exertion on the thumb wheels and return spring means urging the worms forwardly toward meshing engagement with the worm gears.

14. In local body heat sensing instrumentation, the combination comprising a. first and second probes each including a tip having a surface shaped for application in heat transfer proximity with a patient's body, the tip consisting of material characterized as electrically insulative and heat conductive, b. electrically energizable means carried by the probes to detect heat transfer between said surface and the source via said material, and c. a carrier for said probes and from which the probes extend in active positions to locate the tips for engaging a human patient's back so as to closely straddle the central spinal column zone, the probes also have retracted positions relative to the carrier, there being isothermal means on the carrier to be contacted by the tips in said retracted positions, d. means to displace the probes between said active and retracted positions, and e. recording means electrically connected with said electrically energizable means.

15. The combination of claim 14 including probe retainer means on the carrier to retain the probes in said retracted positions.

16. In instrumentation for sensing differential heating of local body areas, the combination comprising a. a pair of probes and means thereon to effect heat transfer between the probes and a patient's body zone toward which the probes are respectively applied, said means including thermistors, the probes including tips embedding the thermistors, the tips consisting of electrically insulative heat conductive material b. a carrier including a housing, and means on the carrier to move the probes between extended positions outside the housing and retracted positions inside the housing, said means including two thumb wheels, and intermeshing worm and worm gear elements operatively connected between each thumb wheel and one of the probes, and c. circuit means electrically connected with said first named means to detect said heat transfer, and recording means connected with said circuit means.

17. In local body heat sensing instrumentation, the combination comprising a. a probe including a tip having a frontwardly exposed surface shaped for application in heat transfer proximity with a patient's body, the tip consisting of material characterized as electrically insulative and heat conductive, b. electrically energizable means carried by the probe to detect heat transfer between said surface and the source via said material, said frontwardly exposed surface being generally convex, c. the probe including an openly hollow and forwardly elongated support, said tip confined at the forward end of said support, said tip having a rearward surface facing and exposed to the hollow interior of the support, the outer extent of the tip connected to the support, said means embedded in the tip material between said front and rear surfaces, d. a carrier carrying said probe and from which the probe extends in active position to locate the tip for engaging a human patient's body, the carrier including a housing, a thumb wheel, and intermeshing worm and worm gear elements operatively connected between the thumb wheel and probe to swing the probe relative to the carrier in response to thumb wheel rotation, and e. recording means electrically connected with said electrically energizable means.

* * * * *